United States Patent [19]

Etzbach et al.

[11] Patent Number: 5,417,884
[45] Date of Patent: May 23, 1995

[54] DEFINED OLIGOMERIC LIQUID-CRYSTALLINE COMPOUNDS HAVING SMECTIC LIQUID-CRYSTALLINE PHASES

[75] Inventors: Karl-Heinz Etzbach; Karl Siemensmeyer, both of Frankenthal; Detlev Joachimi; Carsten Tschierske, both of Halle/Saale; Olaf Agert, Sondershausen, all of Germany

[73] Assignee: BASF Aktiengesellschaft, Ludwigshafen, Germany

[21] Appl. No.: 86,027

[22] Filed: Jul. 6, 1993

[30] Foreign Application Priority Data

Jul. 22, 1992 [DE] Germany .................. 42 24 083.2

[51] Int. Cl.$^6$ .................. C09K 19/34; C09K 19/52; C07D 285/12
[52] U.S. Cl. ................ 252/299.61; 252/299.01; 548/136
[58] Field of Search .......... 252/299.01, 299.61, 252/299.62, 299.63, 299.64, 299.65, 299.66, 299.67; 548/136

[56] References Cited

U.S. PATENT DOCUMENTS 4,966,726 10/1990 Scherowsky et al. ........... 252/299.6
4,997,591 3/1991 Heppke et al. ................ 252/299.61

FOREIGN PATENT DOCUMENTS 504660 9/1992 European Pat. Off. .
2188048 9/1987 United Kingdom .
WO91/16295 10/1991 WIPO .

OTHER PUBLICATIONS

Akopova et al., J. of Gen. Chem. (USSR), vol. 57, No. 3, Mar. 1987, pp. 570–574.
Eidenschink et al., Liquid Crystals, vol. 8, No. 6, 1990, pp. 879–884.
Barclay et al., Macromolecules, vol. 25, No. 11, May 25, 1992, pp. 2947–2954.

Primary Examiner—Shean C. Wu
Attorney, Agent, or Firm—Keil & Weinkauf

[57] ABSTRACT

Liquid-crystalline compounds of the formulae I and II;

$$Z^1-(X^1-R^1-y-M)_m \qquad \text{I}$$

$$Z^2-(X^2-R^1-Y-M)_n \qquad \text{II}$$

where $Z^1$ is the radical of an m-valent alcohol an m-valent acid or certain trivalent triazine derivatives; $Z^2$ is an n-valent radical of a monocyclic or polycyclic aromatic compound; $X^1$ is a chemical bond or -CO-; $X^2$ is -O-, -S-, -CO-O-, -O-CO-, -SO$_2$-, -SO$_2$-O-, -O-SO$_2$-O-, -NR$^4$-, -CO-NR$^4$-, -NR$^4$-O- or -CO-N<, where $R^4$ is H or C$_1$-C$_8$-alkyl; m and n are 3 to 6; $R^1$ is a C$_2$-C$_{20}$-bridge having 2 to 12 bridging members, which may be interrupted by -O-, -S- or -NR$^4$-, each of these hetero units being separated by at least 2 carbon atoms; Y is a chemical bond, -O-, -S-, -CO-O-, -O-CO-, -NR$^4$-, -CO-NR$^4$- or -NR$^4$-CO-; M is a mesogenic group. These compounds are suitable for the production of optical and electro-optical data carriers and display elements.

4 Claims, No Drawings

DEFINED OLIGOMERIC LIQUID-CRYSTALLINE COMPOUNDS HAVING SMECTIC LIQUID-CRYSTALLINE PHASES

The present invention relates to defined oligomeric liquid-crystalline compounds having smectic liquid liquid-crystalline phases of the formulae I and II

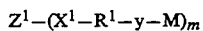  I

  II where $Z^1$ is the alcoholate or acid radical $Z^{1/1}$ of an m-valent aliphatic alcohol or of an m-valent aliphatic carboxylic acid having 3-to 30 carbon atoms; the alcoholate or acid radical $Z^{1/2}$ of an m-valent cycloaliphatic alcohol or of an m-valent cycloaliphatic carboxylic acid having 5 or 6 ring members; in the case where m=3, the nitrogen-containing radical $Z^{1/3}$

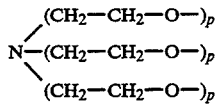

where p may be 1 or 2; in the case where m =3, a radical having the structure $Z^{1/4}a-d$

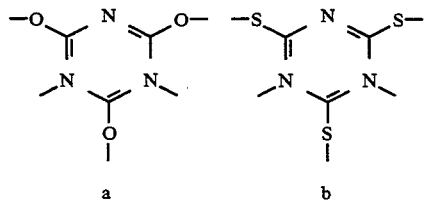

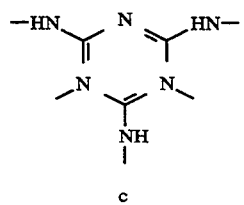

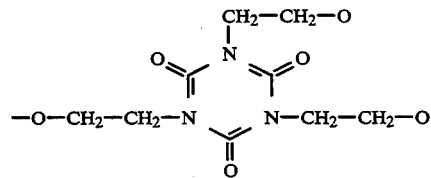

in the case where m=3 or m=4, the acid radical $Z^{1/5}$ of nitrilotriacetic acid or of ethylenediamine-tetraacetic acid;

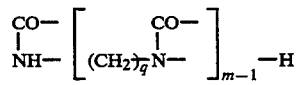

where q may be 2 or 3; is the n-valent radical $Z^{2/1}$ of a benzene

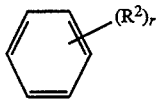

where $R^a$ may be halogen, cyano, nitro, $C_1$ to $C_{10}$-alkyl, $C_1$- to $C_{10}$-alkoxy, $C_1$- to $C_{10}$-alkoxycarbonyl, $C_1$- to $C_{10}$-acyloxy or radicals which are bonded to a ring in the vicinal position, r is zero to 3, and the radicals $R^2$, in the case where r>1, may be identical or different; the polycyclic radical $Z^{2/2}$

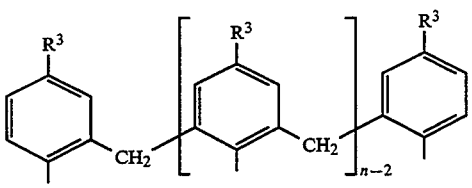

where $R^3$ may be $C_1$- to $C_4$-alkyl, $C_1$- to $C_4$-alkoxy or halogen; in the case where n=3, the phosphorus-containing radical $Z^{2/3}$

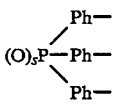

where s may be zero or 1;
$X^1$ is a chemical bond or -CO-;
$X^2$ is oxygen, sulfur, -CO-O-, -O-CO-, -SO$_2$-, -SO$_2$-O-, -O-SO$_2$-O-, -NR$^4$-, -CO-NR$^4$-, -NR$_4$-O- or -CO-N<, where $R^4$ may be hydrogen or $C_1$- to $C_8$-alkyl, with the proviso that, in the case of the polycyclic radical $Z^{2/2}$, $X^2$ can only be -O- or -O-CO-;
m is 3 to 6, with the proviso that m is less than or equal to the number of carbon atoms in $Z^1$;
n is 3 to 6;
$R^1$ is a $C_2$- to $C_{20}$-bridge containing 2 to 12 bridging members, which may be interrupted by oxygen, sulfur or -NR$^4$- it being possible for each of these hetero units to be separated by at least 2 carbon atoms;
Y is a chemical bond, oxygen, sulfur, -CO-O-, -O-CO-, -NR$^4$-, -CO-NR$^4$- or -NR$^4$-CO-, and
M is a mesogenic group derived from a compound which, in the liquid-crystalline phase, has an anisotropy of the dielectric constant $\epsilon$ where $|\Delta\epsilon|>0.3$ and/or which is optically active.

The invention also relates to processes for the preparation of the compounds I and II, and to the use thereof in the form of solid or liquid-crystalline, optically anisotropic media for the display and storage of information.

Liquid-crystalline compounds are optically anisotropic substances which, in contrast to liquids, have a long-range order of the molecules, it being possible for the molecules to have a regular one- or two-dimensional arrangement and to form liquid-crystalline mesophases. With respect to the spatial arrangement of the molecular units within the liquid crystal, a distinction is made between essentially 3 phases: - the nematic phase, - the cholesteric phase and - the smectic phase.

In nematic phases, the individual molecules are aligned in one direction. Their structural feature is a parallel alignment of the molecular long axes at the same time as a random distribution of the molecular centers of gravity. The molecules have no lateral cohesion; there is therefore no layer structure as in the smectic phases described below. The molecules can move relative to one another along their long axes, ie. they can slip past one another freely, which causes their low viscosity. Nematic phases therefore have much lower viscosity than smectic phases.

The structure of the cholesteric phase, which can only be achieved with optically active molecules, is closely related to that of the nematic phase. It is therefore frequently also known as the chiral nematic phase. As in the nematic phase, the molecular long axes of the liquid-crystalline compounds are aligned parallel to one another within a quasi-nematic layer (layer perpendicular to the helix axis), but the preferential direction of the molecular long axes changes regularly through a certain angle from one quasi-nematic layer to the adjacent one. Within an individual layer, a uniform preferential direction exists which is twisted in the same direction through a constant angle with respect to the preferential direction within the adjacent layer. A helical arrangement of the molecular long axes thus forms over a plurality of layers. The helical structure is caused by the chirality of the participating molecules.

Smectic phases have a two-dimensional structure. Intermolecular interactions cause the elongate, rod-like molecules aligned parallel to one another to form layers, which are stacked at identical separations from one another. Various modifications can occur here, differing in the arrangement of the molecules within the layers. Smectic phases $S_A$ to $S_I$ are known. For example, the centers of gravity of the molecules can be arranged randomly ($S_A$ and $S_C$ phases) or regularly (eg. $S_B$ phase) within a layer. The molecular long axes can be parallel or tilted to the perpendiculars on the layer plane. The molecules cannot leave the layer plane since virtually no interactive forces exist between the ends of the molecules. Although this allows the layers to move slightly relative to one another, the more highly ordered state (two-dimensional structure) means that the viscosity of smectic phases is greater than for nematic phases.

Furthermore, smectic liquid-crystalline phases are known which have an electrical spontaneous polarization in the absence of an external electrical field. This polarization can be reoriented by applying an external electrical field; these phases are hence known as ferroelectric smectic liquid-crystalline phases. A typical example is the chiral $S_C$ phase ($S_C^*$ phase). Due to their anisotropic optical and dielectric properties, they can be utilized for electro-optical display elements (abbreviated to displays). Thus, ferroelectric displays based on $S_C^*$ phases allow extremely rapid writing and deletion of symbols.

The following symbols characterize liquid-crystalline phases or liquid-crystalline behavior:

S denotes a smectic liquid-crystalline phase or smectic liquid-crystalline behavior, $S_A$ symbolizes a smectic A phase, in which the molecules are arranged in layers and the layer normal is parallel to the preferential direction of the molecular long axes, $S_C$ symbolizes a smectic C phase, in which the molecules are arranged in layers and the layer normal forms an angle to the preferential direction of the molecular long axes, the tilt angle $\theta$, N denotes a nematic liquid-crystalline phase or nematic liquid-crystalline behavior, N* denotes a cholesteric (chiral nematic) liquid-crystalline phase or cholesteric (chiral nematic) liquid-crystalline behavior, where

* means that the liquid-crystalline compound contains a chiral, ie. optically active, center and it is therefore possible for optically active liquid-crystalline phases to form.

When a solid liquid-crystalline compound melts, a smectic phase, for example, is formed first as a liquid-crystalline phase; as the temperature is increased further, this is converted either into a further liquidcrystalline phase, for example a nematic phase, or, at the clearing point, into the optically isotropic melt, at phase-transition temperatures which are characteristic of each compound. When the melt is cooled, the liquidcrystalline phases and finally the crystal as a solid modification re-form at the corresponding transition temperatures. This interconversion of the liquid-crystalline compound is known as enantiotropic conversion.

Liquid-crystalline compounds are found both amongst low-molecular-weight organic compounds and amongst polymeric organic compounds. In known polymeric liquid crystals, polyacrylic and polymethacrylic chains, inter alia, serve as the main polymer chains. Structural units of low-molecular-weight liquid-crystalline compounds as side groups are linked to this polymer backbone via polymer-analogous reactions.

EP-B 90 282 discloses polymers based on esters and amides of acrylic acid and methacrylic acid which formliquid-crystalline phases. The side chains linked to the main polymer chain via the ester and amide functions comprise a flexible, long-chain moiety which maintains the separation (also known as a spacer) and a mesogenic group or pleochroic dye and affect the formation of liquid-crystalline phases.

Suitable spacers are alkylene groups having 2 to 12 carbon atoms which may be linear or branched and may be interrupted by oxygen, sulfur and/or $R^6$-N< groups where $R^6$ is hydrogen or substituted or unsubstituted alkyl.

Examples of mesogenic groups are those mentioned, for example, in Kelker and Hatz, Handbook of Liquid Crystals, Verlag Chemie 1980, pages 87 to 113.

Depending on the spacers and/or mesogenic groups, the polymers may form liquid-crystalline phases and can be employed alone or together with low-molecular-weight liquid crystals in electro-optical displays.

In principle, the electro-optical displays comprise a 1 to 30 μm liquid-crystalline layer between two glass plates, each of which is coated on the inside with an electrode layer and at least one of which must be transparent. The transparent, electroconductive top layers used are in particular antimony-doped tin oxide layers and tin oxide-doped indium oxide layers.

German Patent Application P 39 17 196.5 discloses monomers of the formula V

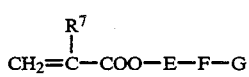

where $R^7$ is hydrogen, chlorine or methyl, E is a flexible spacer, F is a mesogenic moiety which is built up from at least three aromatic rings linked in a linear or approximately linear manner and which contains at least one 2,6-naphthylene group, and G is an optically active chiral moiety. These monomers are used to prepare polymers containing chiral mesogenic side groups with a ferroelectric smectic liquid-crystalline behavior.

A disadvantage of using polymeric liquid crystals is the slow speed of the switching processes, which are in the upper millisecond range to the seconds range (nematic polymers) or in the lower to middle millisecond range (ferroelectric $S_C^*$ polymers). A further disadvantage is that polymeric liquid crystals, unlike low-molecularweight compounds, cannot be synthesized in a uniform, defined molecular weight. The reproducible preparation of these materials is thus a considerable synthetic problem.

However, an advantage for the use of polymeric liquid crystals in display applications is the high mechanical loadability of the LC polymers compared with low-molecular-weight liquid crystals. This is due to the significantly higher viscosity of polymeric LCs.

DE-A 38 27 603 discloses chiral, smectic liquidcrystalline compounds of the formula VI $$M_1^*\text{-}K\text{-}M_2^* \qquad \text{VI}$$

where $M_1^*$ and $M_2^*$ are identical chiral, smectogenic groups, and -K- is a divalent group. They have the property of simultaneously solidifying from the liquid-crystalline phase on cooling to give glass-like materials.

DE 40 11 812 describes tetra-substituted methanes having liquid-crystalline properties. These form nematic phases above the crystalline phase. Due to their low dielectric anisotropy, these materials cannot be realigned by means of an electric field.

It is an object of the present invention to provide liquid-crystalline compounds which have high dielectric anisotropy, high flow viscosity and low rotational viscosity and thus have high mechanical stability, and are compatible with common liquid-crystalline mixtures.

We have found that this object is achieved by the liquid-crystalline compounds I and II defined at the outset.

We have furthermore found various processes, described below in greater detail, for the preparation of the liquid-crystalline compounds I and II, and that these compounds can be used alone, in mixtures with one another and with other liquid-crystalline and/or non-liquidcrystalline compounds in the form of solid or liquidcrystalline, optically anisotropic media for the display and storage of information.

The liquid-crystalline compounds described by the formulae I and II

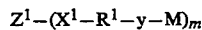

are based on central units denoted by $Z^1$ and $Z^2$. $X^1$ is a chemical bond or -CO-, and $X^2$ is, very generally, a hetero unit which, like $X^1$ is bonded to a $C_2$- to $C_{20}$-bridge which is described by $R^1$ and is known as a spacer. Y is in turn a chemical bond or a hetero unit, and M is a mesogenic group derived from a compound which, in the liquidcrystalline phase, has an anisotropy of the dielectric constant $\epsilon$ where $|\Delta\epsilon| > 0.3$ and/or which is optically active.

m is a number from 3 to 6, with the proviso that m is less than or equal to the number of carbon atoms in $Z^1$; n is a number from 3 to 6.

The central unit $Z^x$ is a radical derived, for example, from the following compounds: from aliphatic alcohols, such as
glycerol,
1,2,4-butanetriol,
2-methyl-2-hydroxymethyl-1,3-propanediol,
2-ethyl-2-hydroxymethyl-1,3-propanediol,
1,2,3,4-butanetetraol,
pentaerythritol,
xylitol,
mannitol and
sorbitol, from aliphatic carboxylic acids, such as
1,2,3-propanetricarboxylic acid,
1,1,4-butanetricarboxylic acid,
1,2,3,4-butanetetracarboxylic acid, citric acid and
2-hydroxynonadecyl-1,2,3-tricarboxylic acid, from cycloaliphatic alcohols having 5 or 6 ring members, such as
1,2,3,4-tetrahydroxycyclopentane,
1,2,3-trihydroxycyclohexane,
1,2,4-trihydroxycyclohexane,
1,3,5-trihydroxycyclohexane,
1,2,3,4-tetrahydroxycyclohexane,
1,2,3,5-tetrahydroxycyclohexane,
1,2,4,5-tetrahydroxycyclohexane,
1,2,3,4,5-pentahydroxycyclohexane and
1,2,3,4,5,6-hexahydroxycyclohexane, from cycloaliphatic carboxylic acids having 5 or 6 ring members, such as
1,2,3-cyclopentanetricarboxylic acid,
1,2,4-cyclopentanetricarboxylic acid,
2-methyl-1,2,3-cyclopentanetricarboxylic acid,
3-methyl-1,2,4-cyclopentanetricarboxylic acid,
1,1,2,2-cyclopentanetetracarboxylic acid,
1,2,2,4-cyclopentanetetracarboxylic acid,
1,1,3,3-cyclopentanetetracarboxylic acid,
1,2,3,4-cyclopentanetetracarboxylic acid,
1,2,3,4,5-cyclopentanepentacarboxylic acid,
1,1,4-cyclohexanetricarboxylic acid,
1,2,4-cyclohexanetricarboxylic acid,
1,3,5-cyclohexanetricarboxylic acid,
1,1,3,3-cyclohexanetetracarboxylic acid,
1,1,4,4-cyclohexanetetracarboxylic acid,
1,2,3,4-cyclohexanetetracarboxylic acid,
1,2,4,5-cyclohexanetetracarboxylic acid,
1,1,3,3,5-cyclohexanepentacarboxylic acid and
1,2,3,4,5,6-cyclohexanehexacarboxylic acid, from alcoholamines, such as triethanolamine,
triisopropanolamine and
aminoethylethanolamine, from triazine derivatives, such as
cyanuric acid,
thiocyanuric acid,
melamine and
trishydroxyethyl isocyanurate, from nitrilotriacetic acid and ethylenediaminotetraacetic acid, and from the radical

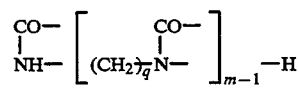

where q may be 2 or 3.

Particularly suitable central units $Z^1$ are glycerol, pentaerythritol, mannitol and citric acid.

The central unit $Z^a$ is an n-valent radical $Z^{2/1}$ of a benzene

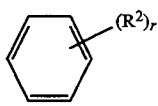

where $R^1$ may be halogen, cyano, nitro, $C_1$- to $C_{10}$-alkyl, $C_1$- to $C_{10}$-alkoxy, $C_1$- to $C_{10}$-alkoxycarbonyl, $C_1$- to $C_{10}$-acyloxy or radicals bonded to a ring in the vicinal position, r is zero to 3, and the radicals $R^2$ in the case where r>1, may be identical or different.

For example, the central unit $Z^2$ is a radical $Z^{2/1}$ derived from a compound such as 1,2,3-trihydroxybenzene,
1,2,4-trihydroxybenzene,
1,3,5-trihydroxybenzene,
1,2,3,4-tetrahydroxybenzene,
1,2,3,5-tetrahydroxybenzene,
1,2,4,5-tetrahydroxybenzene,
hexahydroxybenzene,
1,2,3-benzenetricarboxylic acid,
1,2,4-benzenetricarboxylic acid,
1,3,5-benzenetricarboxylic acid,
3,4,5-trihydroxybenzoic acid,
methyl 3,4,5-trihydroxybenzoate,
1,2,3-trihydroxytoluene,
2,4,5-trihydroxytoluene,
2,4,6-trihydroxytoluene,
3,4,5-trihydroxytoluene,
pyromellitic anhydride,
1,2,3,4-tetrahydroxynaphthalene,
2,3,4-trihydroxyanthracene,
1,2,3-trihydroxy-9,10-anthraquinone and
1,2,4-trihydroxy-9,10-anthraquinone.

$Z^2$ is furthermore a polycyclic radical $Z^{2/2}$ of the formula

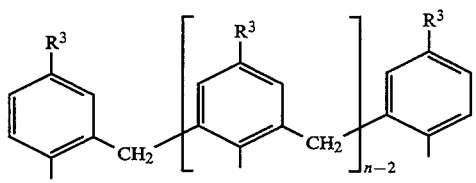

where $R^3$ may be $C_1$- to $C_4$-alkyl, $C_1$- to $C_4$-alkoxy or halogen.

In the case where n=3, the central unit $Z^{1/3}$ may be the phosphorus-containing radical

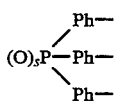

where s may be zero or 1.

Preferred compounds are 1,3,5-trihydroxybenzene, pyromellitic anhydride and methyl 3,4,5-trihydroxybenzoate, and the radical

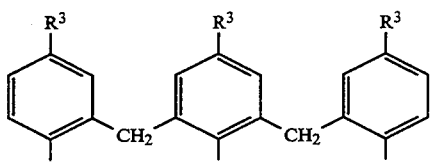

$X^2$ is essentially a hetero unit oxygen, sulfur, -CO-O-, -O-CO-, -$SO_2$-, -$SO_2$-O-, -O-$SO_2$-O-, -$NR^4$- -CO-$NR^4$- -$NR^4$-O- or -CO-N<, where $R^4$ may be hydrogen or $C_1$- to $C_8$- alkyl, with the proviso that, in the case of a polycyclic radical $Z^{1/2}$, $X^2$ can only be -O- or -O-CO-.

Preference is given to oxygen, -CO-O- and -O-CO-.

$R^1$ is a $C_2$- to $C_{20}$-bridge having 2 to 12 bridging members which may be interrupted by oxygen, sulfur or -$NR^4$- it being possible for each of these hetero units to be separated by at least 2 carbon atoms.

Examples of highly suitable bridging members $R^1$ are

—$(CH_2)_2$—, —$(CH_2)_3$—, —$(CH_2)_4$—, —$(CH_2)_5$—,

—$(CH_2)_6$—, —$(CH_2)_7$—, —$(CH_2)_8$—, —$(CH_2)_{10}$—,

—$(CH_2)_{12}$—, —$(CH_2—O—CH_2)_2$—,

—$(CH_2)_2$—S—$(CH_2)_2$—$(CH_2)_2$—N—$(CH_2)_2$— and
$\phantom{aaaaaaaaaaaaaaaaaaaaaaaaaaa}|$
$\phantom{aaaaaaaaaaaaaaaaaaaaaaaaaaa}CH_3$ —CH—$CH_2$—.
$\phantom{aa}|$
$\phantom{aa}CH_3$ Particularly highly suitable bridging members $R^1$ are -$(CH_2)_5$-, -$(CH_2)_6$-, -$(CH_2)_7$- and -$(CH_2)_{10}$-.

Y is a chemical bond, oxygen, sulfur, -CO-O-, -O-CO-, -$NR^4$-, -CO-$NR^4$- or -$NR^4$-CO-, where $R^4$ may be hydrogen or $C_1$- to $C_8$-alkyl.

Oxygen is particularly preferred.

Highly suitable mesogenic groups M are groups of the formula III

-A-(B-A-)$_r$-B$_r$-(D$^1$)$_u$   III where A is 1,4-phenylene or 1,3,4-thiadiazole or 1,3,4oxadiazole or 1,4-cyclohexylene. 1,4-Phenylene and 1,4-cyclohexylene may contain up to two of the hetero atoms oxygen, sulfur and nitrogen, with the proviso that the hetero atoms oxygen and sulfur must not be adjacent.

Furthermore, 1,4-phenylene and 1,4-cyclohexylene may be up to disubstituted by Cl, Br, F, CN or $NO_2$, B is a chemical bond or one of the following bridging members:

—CO—O—, —O—CO—, —$CH_2$—$CH_2$—,

—$CH_2$—O—, —O—$CH_2$—, —$CH_2$—S—, —S—$CH_2$—,

—C≡C—, —CH=CH—, —CH=N—, —N=CH—,

—N=N—, —N=N—,
$\phantom{aaaaaaaaaa}\downarrow$
$\phantom{aaaaaaaaaa}O$ $D^1$ is an -O-CO-$R^5$ or -CO-O-$R^5$ substituent, where $R^5$ is linear $C_1$- to $C_{20}$-alkyl, which may be interrupted by oxygen and may be asymmetrically substituted by fluorine, chlorine, bromine, cyano or methyl, t is a number from 1 to 4, with the proviso that A and B may be different from one another, and u is 1 if $D^1$ is linked to an aromatic ring and 1 or 2 if $D^1$ is linked to a cyclohexylene ring.

Preferred mesogenic groups M are

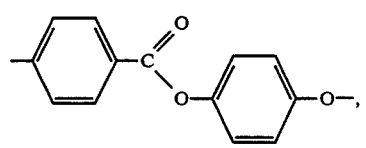
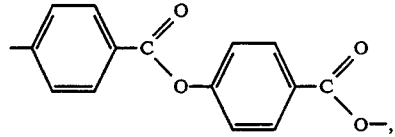
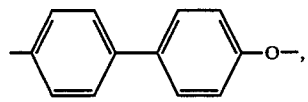
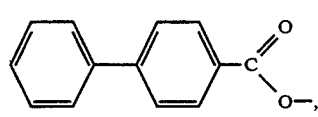
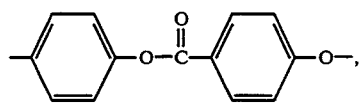
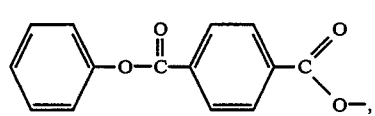
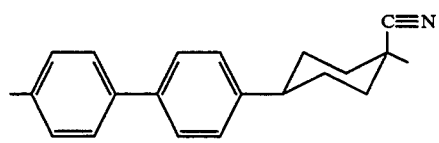
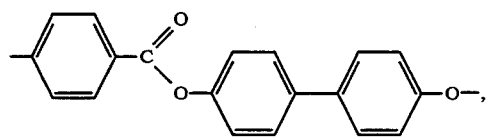
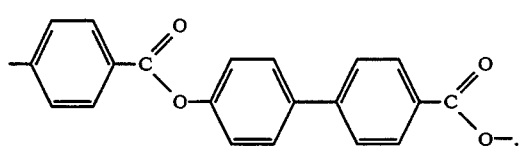
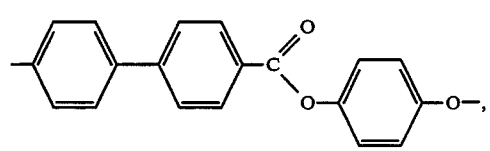
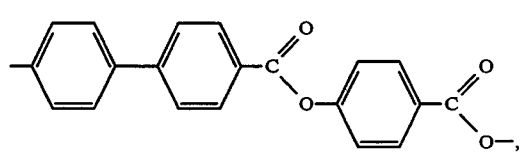

-continued

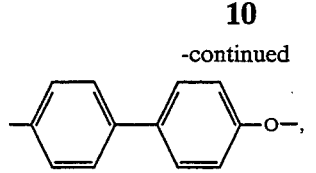
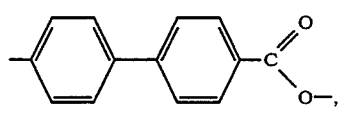
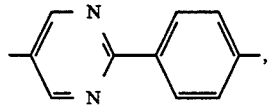
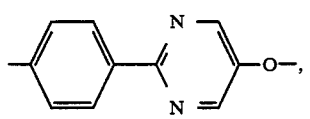
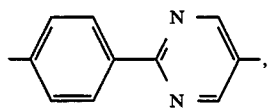
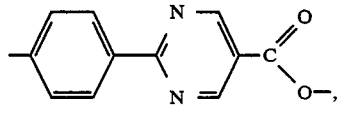
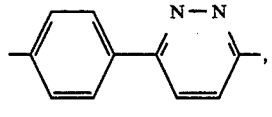
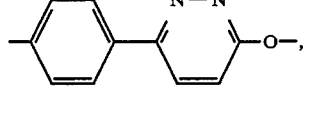
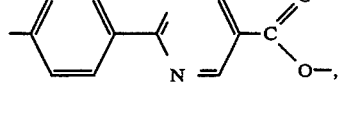

Other highly suitable mesogenic groups M are groups of the formula IV $$B\text{-}A\text{-}(B\text{-}A\text{-})_r\text{-}B\ (D^2)_u \qquad\qquad IV$$

where $D^2$ is one of the following enantiomeric groups: linear $C_1$- to $C_{20}$-alkyl, which may be interrupted once by -COO- or -OCO- or up to twice by -O-, linear $C_1$- to $C_{20}$-alkyl which is asymmetrically substituted on one or two carbon atoms by fluorine, chlorine, bromine, cyano, trifluoromethyl or methyl and may be interrupted once by -CO-O- or up to twice by -O-, or linear $C_3$- to $C_6$-alkyl which is interrupted by

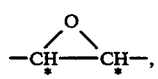

with the proviso that these enantiomeric groups $D^2$ may be linked to A via -O-, -CO-O- or -O-CO-.

Examples of highly suitable enantiomeric groups $D^2$ are:

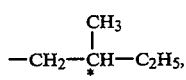  D²/1
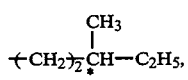  D²/2
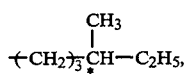  D²/3
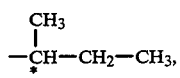  D²/4
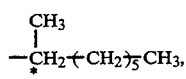  D²/5
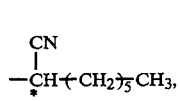  D²/6
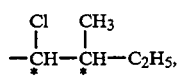  D²/7
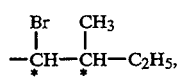  D²/8
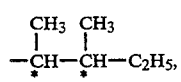  D²/9
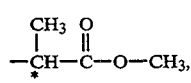  D²/10
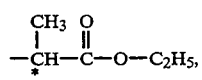  D²/11
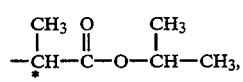  D²/12
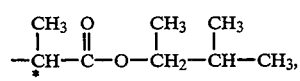  D²/13
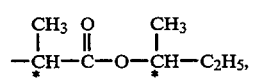  D²/14
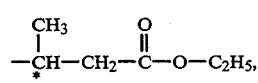  D²/15
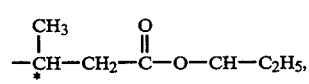  D²/16
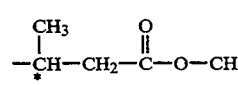  D²/17

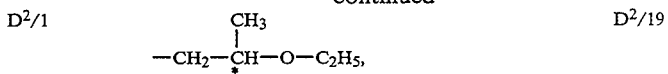  D²/18

-continued

  D²/19

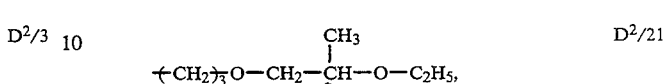  D²/20

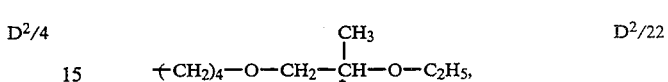  D²/21

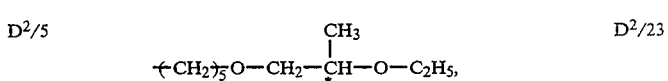  D²/22

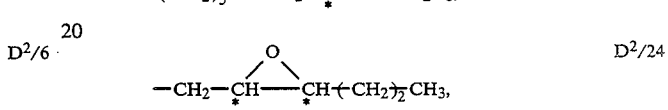  D²/23

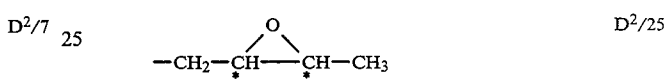  D²/24

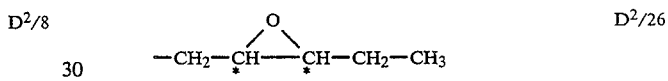  D²/25

-CH₂-CH-O-CH-CH₃  D²/26
      \O/

$\fparen{CH_2}_{\overline{v}}H$,  D²/27 where v=4 to 15 of which D²/6, D²/7, D²/11, D²/15, D²/17 to D²/21, D²/24 and D²/27 are particularly suitable.

Preferred mesogenic groups are

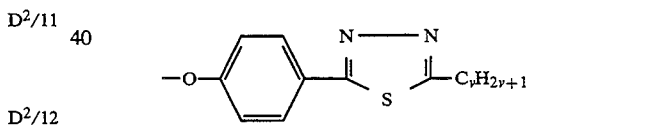

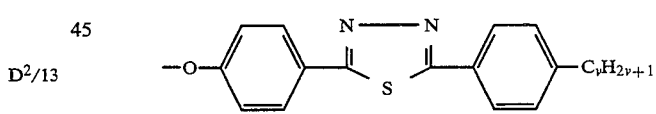

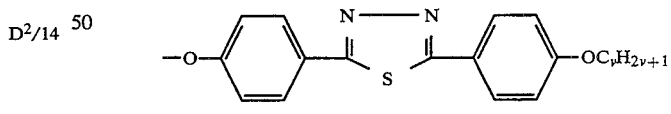

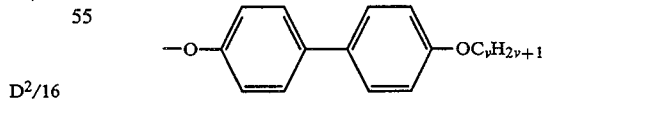

For the preparation of the liquid-crystalline compounds I, the general principle is to react alcohols $Z^1(H)_m$ with carboxylic acid halides M-Y-R¹-CO-Hal where Hal is chlorine or bromine, or carboxylic acids $Z(H)_m$ or derivatives thereof, such as acid chlorides $Z^1(Cl)_m$ or anhydrides $(Z^1)_2O$ with alcohols M-Y-R¹-OH.

In detail, the liquid-crystalline compounds I are obtainable by the following methods:

A carboxylic acid M-Y-R$^1$-COOH is reacted in a known manner with thionyl chloride in the presence of dimethylformamide to give the carboxylic acid chloride M-Y-R$^1$-CO-Cl. In the next step, reaction of the acid chloride M-Y-R$^1$-CO-Cl with an alcohol Z$^1$(H)$_m$ in the presence of pyridine gives the compound I.

Alcoholysis of carboxylic acid chlorides is known in general terms in numerous variants, so that further details in this respect are superfluous. It should merely be added that it is usually advisable to employ the acid chloride in excess in order to react the alcohol quantitatively. After the product I has been isolated, additional purification by means of gel chromatography and subsequent recrystallization can be carried out, for which purpose methylene chloride and/or methanol mixtures are usually suitable.

A further way of preparing the liquid-crystalline compound I is acid-catalyzed esterification of carboxylic acids U$^1$(H)$_m$, acid chlorides Z$^1$(Cl)$_m$ and anhydrides (Z$^1$)$_2$O using alcohols M-Y-R$^1$-OH.

Esterification is known in general terms in numerous variants with respect to the acid, temperature and reaction time.

One variant for the reaction of Z$^1$(H)$_m$ with carboxylic acid chlorides is the reaction with ω-bromocarboxylic acid chlorides Br-R$^1$-CO-Cl and subsequent etherification of the intermediate Z$^1$-CO-R$^1$-Br using an alcoholic compound HO-M to give the compound I.

The general principle for the preparation of the liquid-crystalline compounds II is to react phenolic compounds Z$^2$(OH)$_n$ with compounds derived from compounds of the M-Y-R$^1$-X$^2$-H type or derivatives thereof, or with an alkyl bromide M-Y-R$^1$-Br.

The compounds II are furthermore obtained in a known manner by reacting the compound Z$^2$(OH)$_n$ with an ω-bromocarboxylic acid chloride Br-R$^1$-CO-Cl via an intermediate Z$^2$(-O-CO-R$^1$-Br)$_n$, which is subsequently etherified using the compound HO-M.

Another way of preparing the compounds II is to esterify carboxylic acids hu 2(COOH)$_n$, acid chlorides Z$^2$(COCl)$_n$ or anhydrides (Z$^2$CO)$_2$ using compounds of the M-Y-R$^1$-OH type; this reaction is carried out in a conventional manner.

The liquid-crystalline compounds I and II according to the invention can be prepared in high purity in a uniform molecular weight, and have high flow viscosity.

The liquid-crystalline compounds I and II according to the invention, alone, in mixtures with one another and with other liquid-crystalline and/or non-liquidcrystalline compounds, are highly suitable in the form of solid or liquid-crystalline, optically anisotropic media for the display and storage of information. In addition, they are suitable for the preparation of anisotropic, solid, optical media for optical components, such as compensators, polarizers, prisms, plates having optical rotation and electro-optical storage displays.

EXAMPLES

The phase transitions were determined under a polarizing microscope (Leitz, Ortholux II Pol BK, Mettler FP 82 HT heating stage, Mettler FP 80 control unit), heating rate 10° C./min, and by DSC measurements (PerkinElmer, DSC-7), heating rate 20° C./min.

The following symbols denote the phases. A phase change takes place at the phase-transition temperatures measured.

| | |
|---|---|
| c = | crystalline |
| g = | glass state |
| n = | nematic |
| ch = | cholesteric |
| s = | smectic |
| i = | isotropic |
| S$_A$ = | smectic A |
| S$_C$ = | smectic C |
| S$_1$ | |
| S$_2$ | |
| s$_x$ | unidentified smectic phases. |
| S$_y$ | |
| S$_2$ | |

The transition temperatures (° C.) of the compounds according to the invention are indicated in each of the examples. The temperatures in parentheses denote monotropic phase transitions. These are taken to mean phase transitions which only proceed in one direction, for example if the liquid-crystalline state can only be achieved by supercooling the melt. The melting point is then higher than the clearing point. Preparation of the liquid-crystalline compounds I.

EXAMPLE 1

Preparation of tri- (ω-bromobutanoyl) glycerides 5 mmol of glycerol, 16.5 mmol of ω-bromocarboxylic acid and 1 . 65 mmol of DMAP (dimethylaminopyridine) are dissolved in 25 ml of absolute chloroform in a 100 ml single-necked flask fitted with magnetic stirrer and septum stopper, and the solution is cooled to 5 ° C. by means of an ice bath. 16.5 mmol of DCC (dicyclohexylcarbodiimide) dissolved in 25 ml of absolute chloroform are then slowly added dropwise by means of a syringe. The mixture is allowed to warm to room temperature and is stirred for about 72 hours. The white precipitate is then filtered off with suction (through a layer of kieselguhr from 2 to 3 cm thick) and washed with chloroform. The filtrate is evaporated on a rotary evaporator, and the residue is purified by chromatography. Eluent: chloroform/methanol 10/0.04 Yield: 96%.

EXAMPLE 2

Preparation of glycerol tri(4-(2-heptyl-1,3,4-thiadiazol-yl)phenoxy)butylcarboxylate,

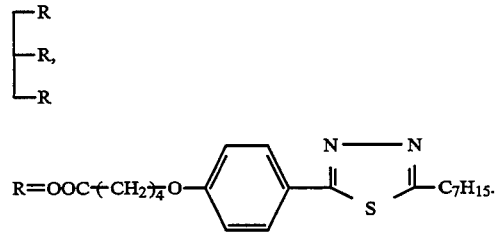

0.5 mmol of tri(ω-bromobutanoyl)glyceride, 1.8 mmol of 4-(2-n-heptyl-1,3,4-thiadiazol-5-yl)phenol, 5 mmol of freshly ignited K$_2$CO$_3$ and 0.5 mmol of KI are dissolved in 20 ml of absolute diethyl ketone or butanone in a 100 ml two-necked flask fitted with reflux condenser and magnetic stirrer, and the mixture is stirred for from 40 to 60 hours under reflux and under a protective gas. When the reaction is complete, the solvent is removed by distillation under reduced pressure, the residue is taken up in chloroform, and the solution is carefully acidified using 10% strength HCl until a clear solution forms. The organic phase is washed a number of times with saturated NaHCO$_3$ solution and subsequently with saturated NaCl solution until neutral and dried over NaSO$_4$, and the solvent is stripped off.

The residue is recrystallized a number of times from absolute ethanol. Yield: 10% Phase behavior: C 81S$_C$98 I.

EXAMPLE 3

Glycerol tri-(4-(2-nonyl- 1,3,4-thiadiazol-5-yl)phenoxy )butylcarboxylate,

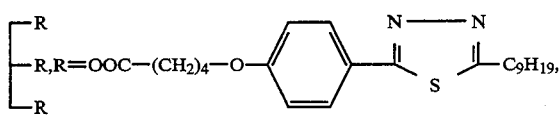

is prepared by methods similar to that of Example 2. Yield: 5% Phase behavior: C 88 S$_C$ 113 I.

EXAMPLE 4

Glycerol tri-(4-(2-pentadecyl-1,3,4-thiadiazol-5-yl)phenoxy)butylcarboxylate,

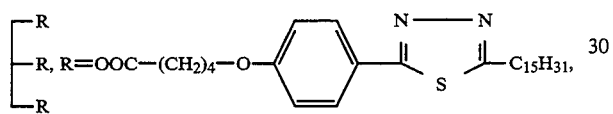

is prepared by methods similar to that of Example 2. Yield: 16.5% Phase behavior: C ? S$_C$ 130 I.

EXAMPLE 5

Glycerol tri-(4-(2-p-octyloxyphenyl-1,3,4-thiadiazol-5-yl)phenoxy)butylcarboxylate,

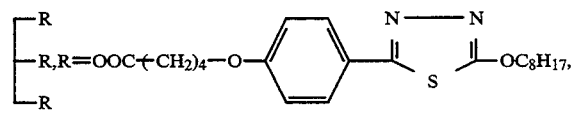

is prepared by methods similar to that of Example 2. Yield: Phase behavior: C 143 S$_C$ 2411.

EXAMPLE 6

Tri(ω-bromoacetyl) glyceride is prepared by methods similar to that of Example 1. Yield: 94%.

EXAMPLE 7

Glycerol tri-(4-(2-nonyl-1,3,4-thiadiazol-5yl)phenoxy)methylcarboxylate,

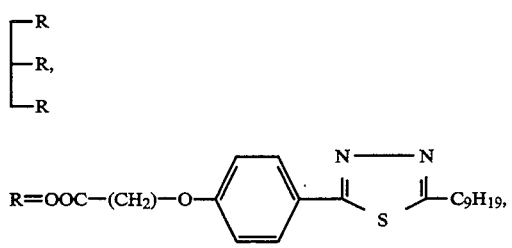

is prepared by methods similar to that of Example 2. Yield: 5% Phase behavior: C 260 S$_x$ 270 Sy 300 Z.

EXAMPLE 8

Tri(ω-bromodecanoyl) glyceride is prepared by methods similar to that of Example 1. Yield: 82%.

EXAMPLE 9

Glycerol tri-(4-(2-nonyl-1,3,4-thiadiazol-5yl)phenoxy)decylcarboxylate,

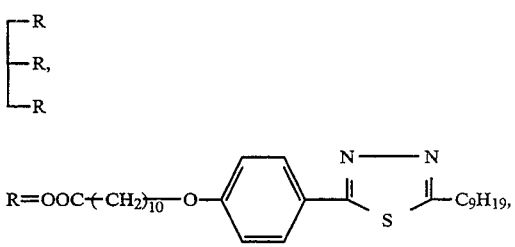

is prepared by methods similar to that of Example 2. Yield: 50% Phase behavior: C? S$_z$ 103 I.

EXAMPLE 10

Glycerol tri-(4-(2-heptyl-1,3,4-thiadiazol-5yl)phenoxy)decylcarboxylate,

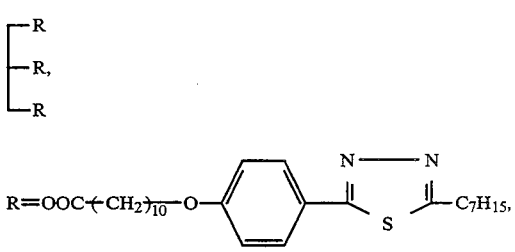

is prepared by methods similar to that of Example 9. Yield: 27.6% Phase behavior: C? S$_z$ 102 I.

EXAMPLE 11

Tetra(ω-bromobutanoyl)pentaerythritol is prepared by methods similar to that of Example 1. Yield: 51%.

EXAMPLE 12

Pentaerythritol tetra(4-(2-nonyl-1,3,4-thiadiazol-5-yl)phenoxy)butyl carboxylate,

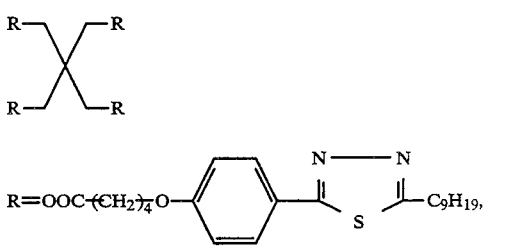

is prepared by methods similar to that of Example 2. Yield: 37.2% Phase behavior: C 121 (S$_C$ 18) I.

EXAMPLE 13

Hexa(ω-bromobutanoyl)mannitol is prepared by methods similar to that of Example 1. Yield: 46.1%.

EXAMPLE 14

Mannitol hexa(4-(2-nonyl-1,3,4-thiadiazol-5-yl)phenoxy)butylcarboxylate,

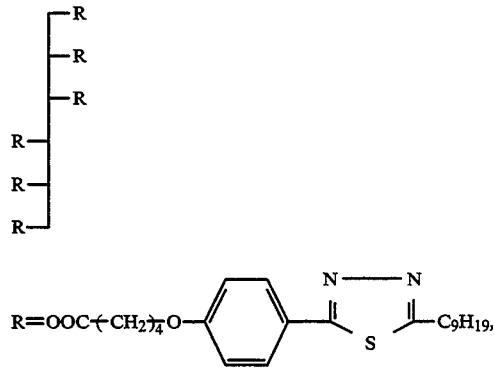

is prepared by methods similar to that of Example 2.

EXAMPLE 15

Preparation of 4-dodecyloxy-4'-(ethoxycarbonylbutyl)biphenyl 30 mmol of dodecyloxybiphenylol, 35 mmol of ethyl bromobutyrate, 30 mmol of freshly ignited potassium carbonate ($K_2CO_3$) and 9 mmol of potassium iodide (KI) are dissolved in 50 ml of absolute diethyl ketone in a 250 ml three-necked flask fitted with reflux condenser and magnetic stirrer, and the mixture is stirred at room temperature for from 60 to 72 hours. When the reaction is complete, the solvent is stripped off, the residue is taken up in chloroform, and the solution is acidified using 10% strength HCl and washed with saturated $NaHCO_3$ solution until neutral. After recrystallization twice from absolute ethanol, the residue is chromatographed using chloroform/ethanol 10/0.08. Yield: 84.7% Melting point: 99° C.

EXAMPLE 16

Preparation of 4-(carboxybutyl)-4'-dodecyloxybiphenyl 19 mmol of the compound from Example 15, 66.7 mmol of KOH, 100 ml of ethanol and 50 ml of water are introduced into a 500 ml single-necked flask fitted with reflux condenser and magnetic stirrer, and the mixture is refluxed for 6 hours. After cooling, the reaction mixture is carefully acidified in concentrated HCl solution and subsequently washed with water until neutral. The solvent is stripped off, and the residue is recrystallized a number of times from glacial acetic acid. The residue is then boiled with methanol and subsequently with ether and filtered off with suction. Yield: 90.5%.

EXAMPLE 17

Preparation of glycerol tri(4-dodecyloxybiphenylolpropyl-carboxylate),

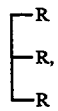

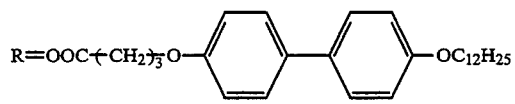

0.8 mmol of glycerol, 2.8 mmol of the compound from Example 16 and 0.28 mmol of DMAP (dimethylaminopyridine) are suspended in 25 ml of absolute chloroform in a 100 ml single-necked flask fitted with magnetic stirrer and septum stopper. 5.76 mmol of DCC (dicyclohexylcarbodiimide) dissolved in 10 ml of absolute chloroform are added dropwise with ice cooling. The mixture is then stirred at room temperature for 72 hours. The white precipitate is then filtered off with suction, the filtrate is evaporated, and the residue is chromatographed (chloroform/glacial acetic acid 10/0.02). The product is then again recrystallized from ethyl acetate. Yield: 6.8% Phase behavior: C 144 $S_A$ 162 I

EXAMPLE 18

Pentaerythritol tetra(4-dodecyloxybiphenylolpropylcarboxylate),

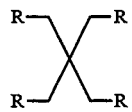

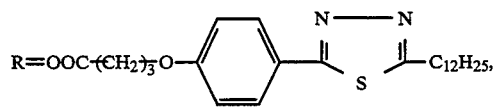

is prepared by methods similar to that of Example 17. Yield: 5.5% Phase behavior: C? $S_1$ 143 $S_2$ 170 $S_A$ 173 I.

We claim:

1. A oligomeric liquid-crystalline compound having a smectic liquid-crystalline phase, of the formula I or II $$Z^1-(X^1-R^1-y-M)_m \quad \quad I$$

$$Z^2-(X^2-R^1-Y-M)_n \quad \quad II$$

where $Z^1$ is the alcoholate or acid radical $Z^{1/1}$ of an m-valent aliphatic alcohol or of an m-valent aliphatic carboxylic acid having 3 to 30 carbon atoms; the alcoholate or acid radical $Z^{1/2}$ of an m-valent cycloaliphatic alcohol or of an m-valent cycloaliphatic carboxylic acid having 5 or 6 ring members; in the case where m = 3, the nitrogencontaining radical $Z^{1/3}$

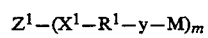
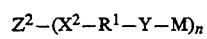
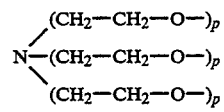

where p may be 1 or 2; in the case where m=3, a radical having the structure $Z^{1/4}$a–d

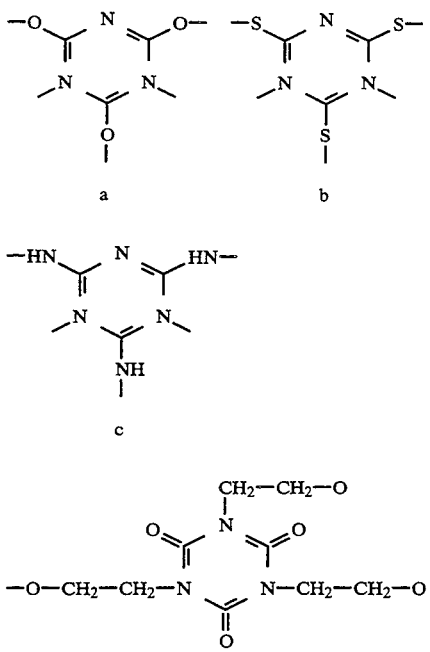

in the case where m=3 or m=4, the acid radical $Z^{1/5}$ of nitrilotriacetic acid or of ethylenediaminetetraacetic acid; the radical $Z^{1/6}$

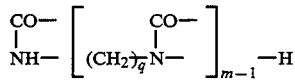

where q may be 2 or 3;

$Z^2$ is the n-valent radical $Z^{2/1}$ of a benzene

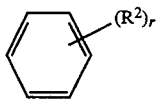

where $R^2$ may be halogen, cyano, nitro, $C_1$ to $C_{10}$-alkyl, $C_1$- to $C_{10}$-alkoxy, $C_1$- to $C_{10}$-alkoxycarbonyl, $C_1$- to $C_{10}$-acyloxy or radicals which are bonded to a ring in the vicinal position, r is zero to 3, and the radicals $R^2$ in the case where r>1, may be identical or different; the polycyclic radical $Z^{2/2}$

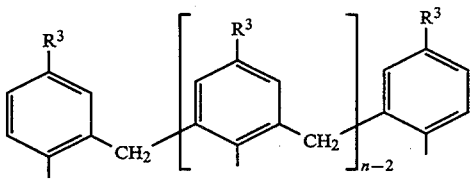

where $R^3$ may be $C_1$- to $C_4$-alkyl, $C_1$- to $C_4$-alkoxy or halogen;

in the case where n=3, the phosphorus-containing radical $Z^{2/3}$

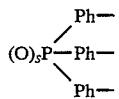

where s may be zero or 1;

$X^1$ is a chemical bond or -CO-, $X^2$ is oxygen, sulfur, -CO-O-, -O-CO-, -SO$_2$-, -SO$_2$-O-, -O-SO$_2$-O-, -NR$^4$-, -CO-NR$^4$, -NR4-O or -CO-N<, where $R^4$ may be hydrogen or $C_1$- to $C_8$-alkyl, with the proviso that, in the case of the polycyclic radical $Z^{1/2}$, $X^2$ can only be -O- or -O-CO-;

m is 3 to 6, with the proviso that m is less than or equal to the number of carbon atoms in $Z^1$;

n is 3 to 6;

$R^1$ is a $C_1$- to $C_{20}$-bridge containing 2 to 12 bridging members, which may be interrupted by oxygen, sulfur or -NR$^4$- it being possible for each of these hetero units to be separated by at least 2 carbon atoms;

Y is a chemical bond, oxygen, sulfur, -CO-O-, -O-CO-, -NR$^4$-, -CO-NR$^4$- or -NR$^4$-CO-, and M is a mesogenic group of the formula III or IV containing at least one 1,3,4-thiadiazolyl radical -A-(B-A-)$_r$-B-(D$^1$)$_u$    III -B-A-(B-A-)$_r$-B-(D$^2$)$_u$    IV where A is 1,4-phenylene or 2,6-naphthalene, which may contain up to two nitrogen atoms as hetero atoms and may carry up to two fluorine, chlorine, bromine, nitro or cyano substitutents, is 1,3,4-thiadiazolyl or is 1,4-cyclohexylene, which may contain up to two hetero atoms from oxygen, sulfur and nitrogen, in each case in nonadjacent positions, B is a chemical bond or one of the following bridging members:

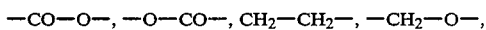

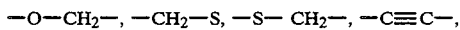

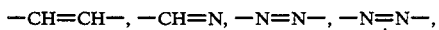

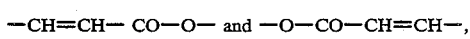

$D^1$ is a fluorine, chlorine, bromine, nitro, cyano, -OCFH$_2$, OCF$_2$H, -OCF$_3$, -O-CO-R$^5$ or -CO-O-R$^5$ substitutent, where $R^5$ is linear $C_1$- $C_{20}$-alkyl, which may be interrupted by oxygen and may be asymmetrically substituted by fluorine, chlorine, bromine, cyano or methyl;

$D^2$ is one of the following enantiomeric groups: linear $C_1$- to $C_{10}$-alkyl which is asymmetrically substituted on one or two carbon atoms by fluorine, chlorine, bromine, cyano, trifluoromethyl or methyl and may be interrupted once by -CO-O- or up to twice by -O-, or linear $C_3$- to $C_6$-alkyl which is interrupted by

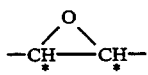

with the proviso that these enantiomeric groups $D^2$ may be linked to A via -O-, -CO-O or -O-CO-, t is a number from 1 to 4, with the proviso that A and B may be different from one another, and u is 1 if $D^1$ is linked to an aromatic ring and is 1 or 2 if $D^1$ is linked to a cyclohexylene ring.

2. The compound of claim 1 wherein M is of the formula III.

3. The compound of claim 1 wherein M is of the formula IV.

4. The oligomeric liquid crystalline compound of claim 1 of the formula:

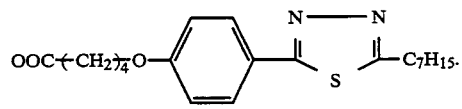

* * * * *

UNITED STATES PATENT AND TRADEMARK OFFICE
CERTIFICATE OF CORRECTION

PATENT NO. : 5,417,884
DATED : May 23, 1995
INVENTOR(S) : ETZBACH et al.

It is certified that error appears in the above-indentified patent and that said Letters Patent is hereby corrected as shown below:

item [57], in the formula "y" should be --Y--.

Column 18, claim 1, line 46, "y" should be --Y--.

Column 19, claim 1, line 51, after "$R^2$" insert a comma --,--.

Column 20, claim 1, line 14, "$Z^1/2$" should be --$Z^2/2$--.

Column 20, claim 1, line 18, "$C_1$" should be --$C_2$--.

Column 20, claim 1, line 47, "$CH_2$-S" should be -- $CH_2$-S- --.

Column 20, claim 1, line 49, between "-CH=N" and "-N=N-" insert -- -N=CH- --.

Column 22, claim 4, after "claim 1 of the formula:" insert --$CH_2$(OR)CH(OR)$CH_2$(OR) wherein R is --.

Signed and Sealed this

Eighth Day of August, 1995

Attest:

BRUCE LEHMAN

*Attesting Officer*  *Commissioner of Patents and Trademarks*